United States Patent
Albrighton et al.

(10) Patent No.: US 9,657,218 B2
(45) Date of Patent: May 23, 2017

(54) PREDICTING PROPERTIES OF WELL BORE TREATMENT FLUIDS

(71) Applicant: Halliburton Energy Services, Inc., Houston, TX (US)

(72) Inventors: Lucas D. Albrighton, Denver, CO (US); Herron J. Kennedy, Brighton, CO (US)

(73) Assignee: Halliburton Energy Services, Inc., Houston, TX (US)

(*) Notice: Subject to any disclaimer, the term of this patent is extended or adjusted under 35 U.S.C. 154(b) by 366 days.

(21) Appl. No.: 13/945,136

(22) Filed: Jul. 18, 2013

(65) Prior Publication Data
US 2015/0024976 A1  Jan. 22, 2015

(51) Int. Cl.
*G01V 11/00* (2006.01)
*C09K 8/60* (2006.01)
*C09K 8/02* (2006.01)
*C09K 8/40* (2006.01)
*C09K 8/42* (2006.01)
*C09K 8/62* (2006.01)
*C09K 8/72* (2006.01)

(52) U.S. Cl.
CPC ............... *C09K 8/601* (2013.01); *C09K 8/02* (2013.01); *C09K 8/40* (2013.01); *C09K 8/424* (2013.01); *C09K 8/62* (2013.01); *C09K 8/72* (2013.01)

(58) Field of Classification Search
None
See application file for complete search history.

(56) References Cited

U.S. PATENT DOCUMENTS

| | | |
|---|---|---|
| 5,285,692 A | 2/1994 | Steiger et al. |
| 6,721,770 B1* | 4/2004 | Morton ............. G06F 17/11 702/104 |
| 7,077,203 B1 | 7/2006 | Roddy et al. |
| 8,122,759 B2 | 2/2012 | Weightman et al. |
| 8,126,689 B2 | 2/2012 | Soliman et al. |
| 8,191,632 B2 | 6/2012 | Lindvig et al. |
| 8,204,724 B2 | 6/2012 | Smart et al. |
| 8,266,949 B2 | 9/2012 | Harris et al. |
| 8,364,253 B2 | 1/2013 | Voth |
| 8,372,789 B2 | 2/2013 | Harris et al. |
| 8,424,368 B2 | 4/2013 | Tonmukayakul et al. |

(Continued)

FOREIGN PATENT DOCUMENTS

WO  0194749  12/2001

OTHER PUBLICATIONS

International Search Authority; Search Report and Written Opinion, Date of mailing: Nov. 10, 2014.

(Continued)

*Primary Examiner* — Jeffrey Washville
(74) *Attorney, Agent, or Firm* — Craig W. Roddy; Tumey L.L.P.

(57) ABSTRACT

Methods and systems for predicting properties of well bore treatment fluids are disclosed. An embodiment includes a method of predicting fluid properties comprising: determining an operational window for a well bore fluid system; collecting data at vertices of the operational window; and developing a model comprising predicted properties for a plurality of data points within the operational window, wherein developing the model uses Barycentric interpolation.

14 Claims, 5 Drawing Sheets

(56) References Cited

U.S. PATENT DOCUMENTS

| | | |
|---|---|---|
| 8,433,150 B2 | 4/2013 | Yuan et al. |
| 2002/0010548 A1* | 1/2002 | Tare ................. E21B 21/08 |
| | | 702/9 |
| 2002/0153137 A1 | 10/2002 | Ziauddin et al. |
| 2007/0007006 A1 | 1/2007 | Massingill et al. |
| 2010/0181073 A1* | 7/2010 | Dupriest ................. C09K 8/03 |
| | | 166/308.1 |
| 2011/0017452 A1 | 1/2011 | Benkley et al. |
| 2012/0267107 A1 | 10/2012 | Benkley et al. |
| 2013/0112405 A1 | 5/2013 | Chatterji et al. |
| 2013/0157903 A1 | 6/2013 | Benkley et al. |

OTHER PUBLICATIONS

Halliburton Brochure entitled "SA-1015™ Suspending Agent," dated Mar. 2012.
Halliburton Brochure entitled "CFR-3™ and CFR-3L™ Dispersant," dated Apr. 2012.
Halliburton Brochure entitled "Tuned Spacer™" Optimized Rheology Spacer, dated Apr. 2007.
Barycentric Interpolation, available at http://classes.soe.ucsc.edu/cmps160/Fall10/resources/barycentricinterpolation.pdf, printed from the Internet on Mar. 6, 2013.
Canadian Office Action for Canadian Application No. 2,913,820 dated Dec. 8, 2016.

* cited by examiner

PREDICTING PROPERTIES OF WELL BORE TREATMENT FLUIDS

BACKGROUND

Well bore treatment fluids often are used in, e.g., well drilling, completion, and stimulation operations. Examples of such well bore treatment fluids include, but are not limited to, drilling fluids, cement compositions, spacer fluids, fracturing fluids, acidizing fluids, completion fluids, and the like. As used herein, the term "well bore treatment fluid" will be understood to mean any fluid that may be used in a subterranean application in conjunction with a desired function and/or for a desired purpose. The term "well bore treatment fluid" does not imply any particular action by the fluid. The well bore treatment fluids may be introduced into a well bore in accordance with known techniques.

It may be desirable to know various properties of the well bore treatment fluids to accurately predict how the fluids should act upon being introduced into the well bore. Fluid properties that may be important when designing well bore treatment fluids include, but are not limited to, rheological behavior, fluid loss, static gel strength, sedimentation, thickening time, compressive strength, viscosity, and free water, among others. A particular fluid may be selected for use in a well bore based on one or more of these properties. For example, a spacer fluid may be selected having a rheology that maximizes the fluid's displacement efficiency. Additionally, optimizing a spacer fluid's rheology can also help to prevent fluid inversion due to fluid density differences between the fluids before and after the spacer fluid. By way of further example, a fracturing fluid may be selected having a viscosity sufficient to generate fracture geometry and transport proppant. The fluid design for a subterranean operation has typically been based on both experience and laboratory testing, whereas the use of modeling methods to predict fluid behavior has been limited. For example, fluid design can require extensive laboratory time to test a number of different fluid formulations before a well bore treatment fluid having desirable properties may be selected.

BRIEF DESCRIPTION OF THE DRAWINGS

These drawings illustrate certain aspects of some of the embodiments of the present invention, and should not be used to limit or define the invention.

DESCRIPTION OF PREFERRED EMBODIMENTS

Embodiments of the present techniques relate to predicting properties, such as rheological properties, of well bore treatment fluids. In accordance with present embodiments, the properties may be predicted with a limited amount of lab testing. Accordingly, costs may be saved and a competitive advantage may be gained by reducing the amount of lab time that may be required to design a fluid for use in subterranean operations. Among other things, embodiments may allow the design of a fluid with minimal customer notice, thus giving the opportunity for reduced rig time, improved bond logs, and/or better customer satisfaction.

Embodiments disclosed herein related to design of a well bore treatment fluid for use in subterranean operations. Subterranean operations in which the well bore treatment fluids may be used include well drilling, completion, and stimulation operations. Examples of such well bore treatment fluids include, but are not limited to, drilling fluids, cement compositions, spacer fluids, fracturing fluids, acidizing fluids, completion fluids, and the like. In some embodiments, methods may employ Barycentric interpolation to develop a model that includes predicted properties such as rheological data for a plurality of data points within the boundaries of a fluid system. A well bore treatment fluid may then be designed using the model. One example of such a well bore treatment fluid is a spacer fluid. Embodiments may be particularly advantageous for spacer fluids due to the fluid rheologies that are typically required when using these fluids. In particular, optimized rheology may be important for spacer fluids, for example, to ensure proper hole cleaning, fluid separation, and efficient fluid recovery and displacement.

An embodiment provides a method of predicting fluid properties comprising: determining an operational window for a well bore fluid system; collecting data at vertices of the operational window; and developing a model comprising predicted properties for a plurality of data points within the operational window, wherein developing the model uses Barycentric interpolation.

Another embodiment provides a method of servicing a well bore comprising: providing an optimized treatment fluid, wherein the optimized treatment fluid is based, at least in part, on a model developed using Barycentric interpolation; and introducing the treatment fluid into a well bore.

Yet another embodiment provides a fluid property prediction system comprising: memory; and a processor coupled to the memory, wherein the processor is configured to receive data for a fluid system and develop a model using Barycentric interpolation, the model comprising predicted properties for a plurality of data points within an operational window of the fluid system.

Figure 1:
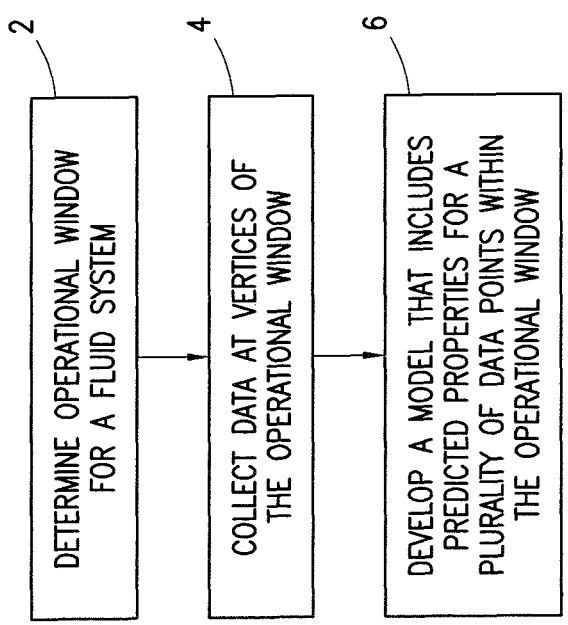
FIG. 1 is a flow chart illustrating an example method for predicting properties of well bore treatment fluids.

FIG. 1 is a flow chart illustrating an example method for predicting properties of well bore treatment fluids. As shown in step 2, the method may include determining an operational window for a fluid system. The method may further include collecting data at vertices of the operational window (step 4). Once the data is collected, a model may be developed (step 6) that includes predicted properties (such as rheological data) for a plurality of data points within the operational window of the fluid system, wherein Barycentric interpolation is used in developing the model.

The operational window generally may define the boundaries of the fluid system. Two or more boundary conditions may be used to determine the operational window. Non-limiting examples of boundary conditions that may be used in developing the operational window include, without limitation, rheology, compressive strength, fluid loss, static gel strength, sedimentation, thickening time, free water, cement mechanical properties (e.g., Young's modulus, Poisson's ratio, specific heat, thermal conductivity, and post-set expansion), wettability, emulsion, break time, pH, post-set permeability, hydration time, post-set porosity, mass or volumetric ratio of an additive (e.g., weighting additive, viscosifier, fluid loss control additive, proppant, etc) to water, additive concentration (e.g., cement set retarder, fluid loss control additive, proppant, crosslinking agent, friction reducer, buffer, surfactant), density, viscosity, temperature, foam quality, permeability, expansion, water properties (e.g., pH, chlorides, bicarbonates, iron, tannin/lignins, carbonates, sulfates, magnesium, and calcium concentration), fluid break time (e.g., for fracturing fluids), and proppant size. In one particular embodiment, the boundary conditions may be ratio of weighting additive to water and ratio of viscosifier to water. In another particular embodiment, the boundary conditions may be temperature and thickening time or free water. Two boundary conditions may be defined for a two-dimensional operational window. For a three-dimensional operational window, three boundary conditions may be defined. In some embodiments, multiple operation windows may be defined and the interpolation may occur across dimensions.

Figure 4:
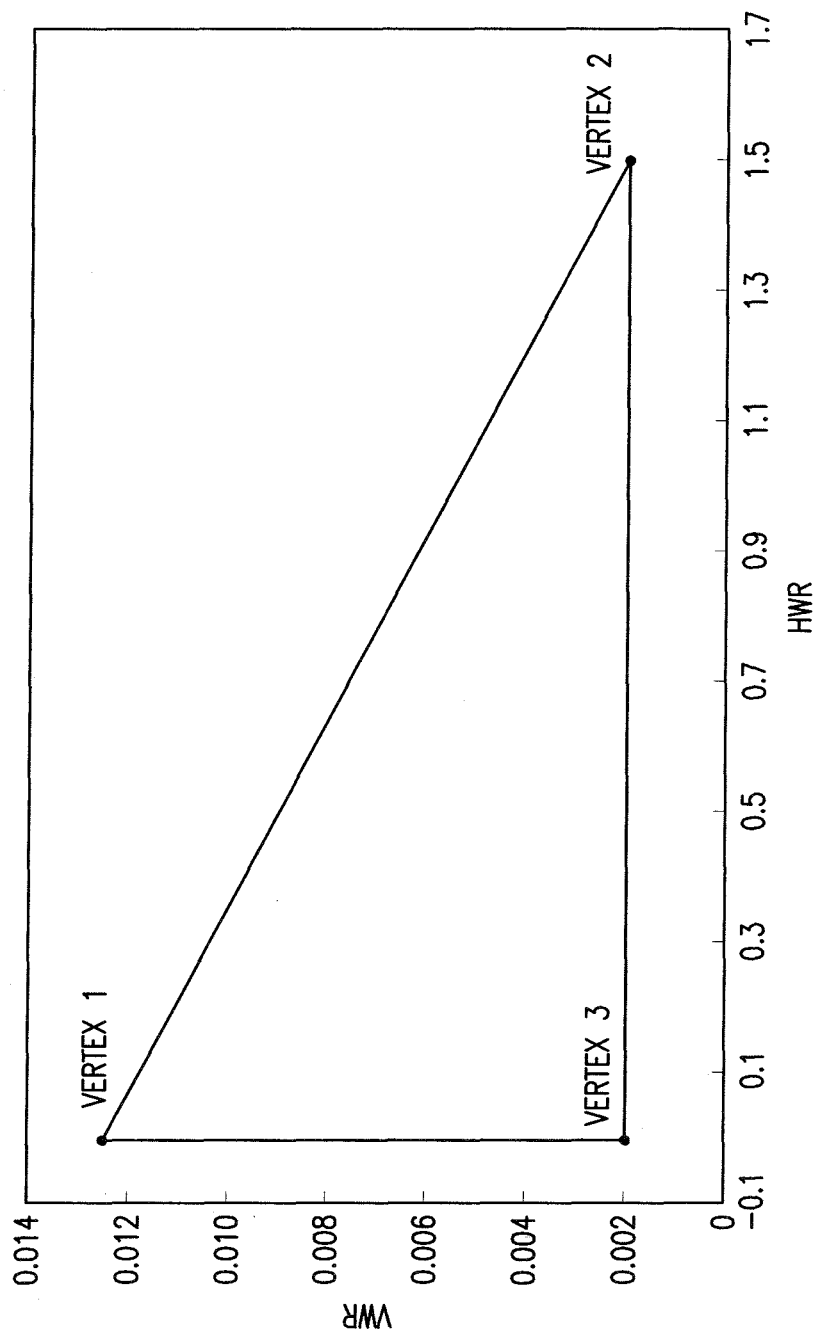
FIG. 4 is an example operational window that may be used in example methods for predicting rheological properties.

Three or more points or vertices may be selected that define the operational window. By way of example, a two-dimensional operational window may be defined as follows: Vertex 1 ($x_1$, $y_1$), Vertex 2 ($x_2$, $y_2$), . . . Vertex n ($x_n$, $y_n$), wherein n is the number of vertices defining the operational window, x is a first boundary condition, and y is a second boundary condition. In some embodiments, the operational window may be a triangular window that is defined by three vertices. FIG. 4 is a graphical representation of an example triangular operational window. FIG. 4 will be described in more detail below. In further embodiments, the boundary conditions at each vertex may be mass ratio of weighting additive to water and mass ratio of viscosifier to water. By way of further example, a three-dimensional operational window may be defined as follows: Vertex 1 ($x_1$, $y_1$, $z_1$), Vertex 2 ($x_2$, $y_2$, $z_2$), and Vertex n ($x_n$, $y_n$, $z_n$), wherein n is the number of vertices defining the operational window, x is a first boundary condition, y is a second boundary condition, and z is a third boundary condition.

In some embodiments, the operational window may be determined based on the functional boundaries of the fluid system. By way of example, the maximum and/or minimum of each boundary condition may be used to define one or more vertices of the operational window. The functional boundaries of a fluid system may be generally defined by the operational limits of a fluid, for example, the limits of the particular boundary conditions for the fluid system. In one embodiment, Vertex 1 may be defined as the maximum viscosifier, Vertex 2 may be defined as the maximum weighting additive, and Vertex 3 may be defined as the minimum viscosifier and minimum weighting/no weighting additive. By way of example, a three-dimensional operational window may be defined as follows, wherein the x-axis is weight ratio of weighting additive and the y-axis is weight ratio of viscosifier to water: Vertex 1 (0, $y_1$), Vertex 2 ($x_2$, $y_2$), Vertex 3 (0, $y_3$), wherein $y_1$ is the maximum weight ratio of viscosifier to water, $x_2$ is the maximum weight ratio of weighting additive to viscosifier, $y_2$ is the minimum weight ratio of viscosifier to water, and $y_3$ is the minimum weight ratio of viscosifier to water. Those of ordinary skill in the art, with the benefit of this disclosure, should be able to determine functional boundaries of a fluid system, for example, using lab testing or other appropriate methodologies.

Figure 5:
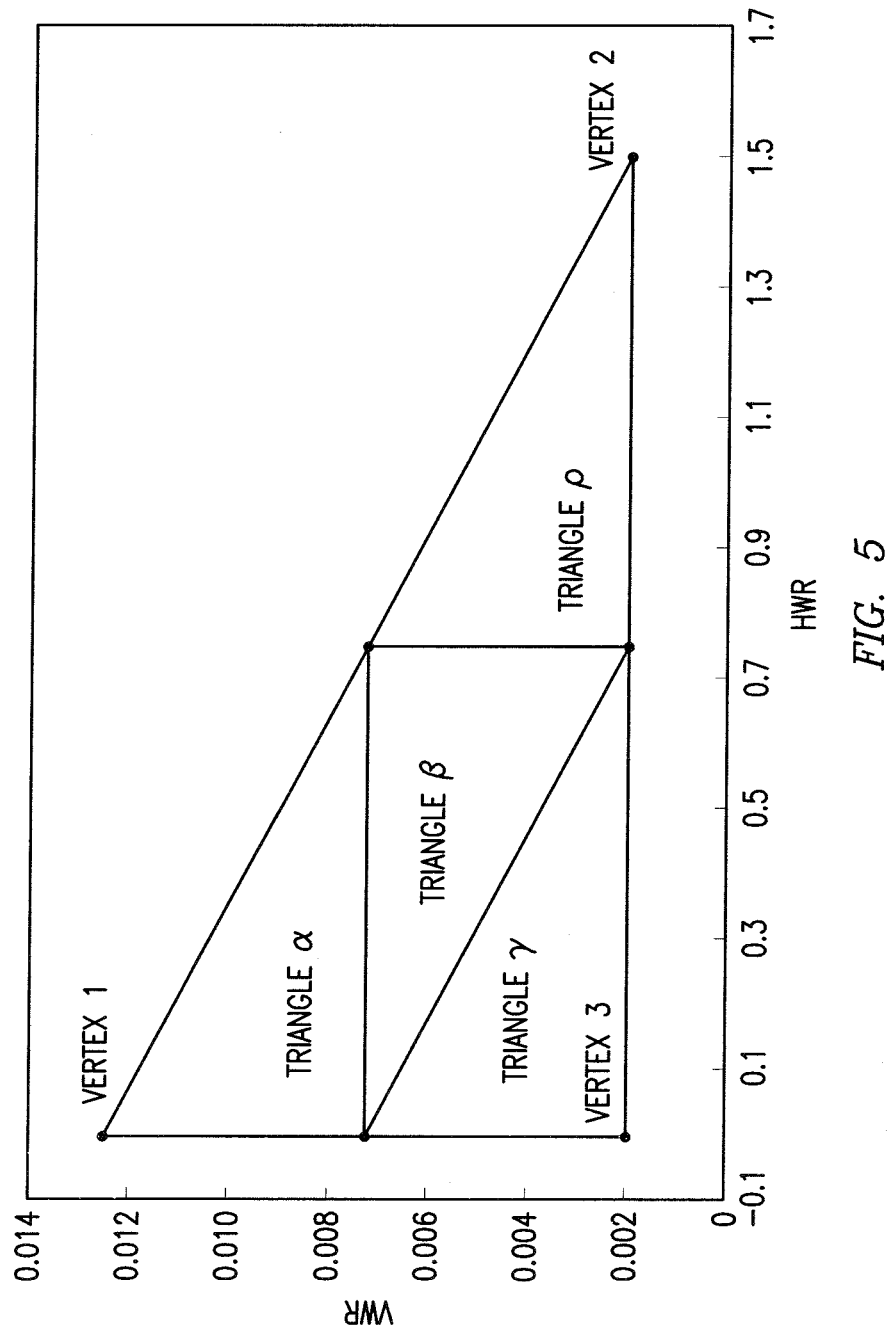
FIG. 5 is another example of an operational window that may be used in example methods for predicting rheological properties.

In some embodiments, the operational window may be divided into two or more sub-windows, for example, to increase the accuracy of the property prediction. By way of example, one or more points may be selected on edges of the operational windows that could be used to divide the operational window into sub-windows. In particular embodiments, the operational window may be divided into two, three, four, five, six, or more sub-windows. FIG. 5 is a graphical illustration of an example operational window that has been divided into four sub-windows. FIG. 5 will be described in more detail below. By dividing the operational window in this manner, the interpolation technique may be refined to increase the accuracy of the resultant property prediction.

As illustrated, the example method at step 4 may include collecting data at vertices of the operational window. In particular embodiments, the collecting the data may include collecting data at vertices of each sub-window that has been created, for example, by division of the operational window. The collected data generally may be related to desirable properties of the fluid system relative to subterranean operations. By way of example, the collected data related to one or more of the following properties: rheology, compressive strength, fluid loss, static gel strength, sedimentation, thickening time, free water, cement mechanical properties (e.g., Young's modulus, Poisson's ratio, specific heat, thermal conductivity, and post-set expansion), wettability, emulsion, break time, pH, post-set permeability, hydration time, post-set porosity. Data may be collected using standard laboratory techniques or other suitable methodologies. In some embodiments, historical data may be used so that additional laboratory testing may not be required.

At step 6, the example method may further include developing a model that includes predicted properties (such as rheological data) for a plurality of data points within the operational window of the fluid system. Each data point may correspond to a fluid having a specific composition, wherein the model predicts properties for the particular fluid represented by that data point. Density may be also determined for each of the data points within the operational window. In some embodiments, methods may employ Barycentric interpolation to develop the model within the operational window. By way of example, Barycentric interpolation may be used to interpolate one or more properties for a plurality data points within the operational window. Embodiments may use Microsoft Excel or other suitable software program may be used to implement disclosed interpolation techniques using a processor, for example. The Barycentric interpolation may use the collected data for the vertices of the operational window (or sub-windows) as the known data points in the interpolation. The interpolation technique may be adjusted to generate any number of data points within operational window. By way of example, the interpolation technique may generate at least 100, at least 1,000, or at least 10,000 data points within the operational window. In additional embodiments, a specific set of results may be determined by determining a specific data point based on entered boundary conditions. By way of example, two or more boundary conditions may be entered and the model may predict properties at those particular boundary conditions.

Once a model has been developed using Barycentric interpolation, for example, the model may be used in selection of a well bore treatment fluid for use in a subterranean operation. By way of example, a well bore treatment fluid may be selected for use in a subterranean operation based on the model. As the model should contain a number of different data points (e.g., density, predicted properties, etc.) for the fluid system, the data points generally represent a set of potential fluids. A user may select a fluid from this set of potential fluids having desirable properties. In some embodiments, the method may include inputting desirable properties wherein the method compares the inputted properties to the predicted properties model to determine one or more potential fluids having optimum properties. By way of example, in response to the comparison, one or more data points (which correspond to potential fluids, for example) may be output. In particular embodiments for spacer fluids, rheology data for the fluid (e.g., a drilling fluid) ahead of the spacer fluid and the fluid (e.g., a cement composition) behind the spacer fluid may be compared to the model to determine one or more potential fluids having optimum properties. In further embodiments, additional properties may be input including, for example, desired density of the fluid, anticipated pump rates, and well geometry. Once the fluid or a set of fluids has been selected, the selected fluid may be further refined, for example, by use of simulation and/or laboratory testing.

In some embodiments, the model may be used to predict properties within the operational window based off a change in density by changing the concentration of water in the fluid system. This may be desirable, for example, to allow for onsite adjustments to a particular well bore fluid at the well site. In particular embodiments, water concentration may be changed at the well site to change the rheology of the fluid.

Figure 2:
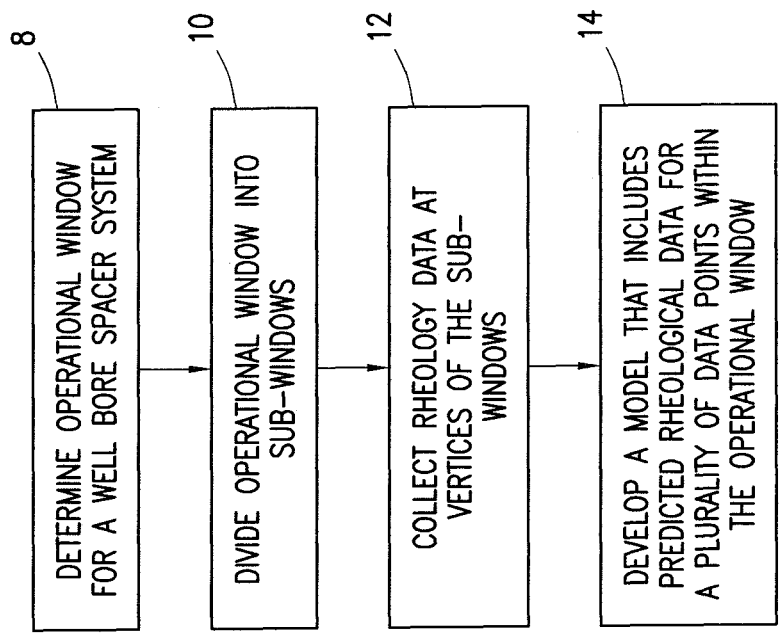
FIG. 2 is a flow chart illustrating an example method for predicting rheological properties of well bore treatment fluids.

FIG. 2 is a flow chart illustrating another example method for predicting properties of well bore treatment fluids. The embodiment illustrated on FIG. 2 relates to prediction of properties for a well bore spacer system. As illustrated on FIG. 2, the method at step 8 may include determining an operational window for a well bore spacer system. The method may further include dividing the operational window into sub-windows at step 10. Rheology data may then be collected at vertices of the sub-windows (step 12). Once the data is collected, a model may be developed, as shown at step 14, that includes predicted rheological data for a plurality of data points within the operational window of the fluid system, wherein Barycentric interpolation is used in developing the model.

In some embodiments, one or more parameters of the well bore spacer system may be pre-defined. In some embodiments, the components of the well bore spacer system may also be pre-defined. By way of example, present embodiments may be used to predict properties of a well bore spacer system having pre-defined components. In some embodiments, relative proportions of certain components may also be pre-defined. Properties may be predicted using a well bore spacer system that comprises, for example, an aqueous component, a weighting additive, and a viscosifier. The well bore spacer system may also comprise one or more of a dispersant, lost circulation material, surfactant, buffer, clay control additive, salt, thixotropic additive, and dye, among others. Heavyweight additives may be included in a spacer fluid to increase the density of the spacer fluid while still maintaining the necessary fluid properties (e.g., fluid rheologies). A spacer fluid having an increased density may be desirable to more precisely match the densities of the drilling fluid and/or cement composition in the well bore. Examples of heavyweight additives that may be used include, but are not limited to, hematite, hausmannite, barite, cement kiln dust, and sand. The viscosifier may be included in the spacer fluid system, for example, to aid in the control of free water and/or for solids suspension. Examples of viscosifiers that may be used include, but are not limited to, guar gums, xanthan gums, diutan gums, carboxymethylhydroxyethyl cellulose, and clays (e.g., bentonite, etc.).

As previously mentioned, the operational window generally may define the boundaries of a fluid system. In the illustrated embodiment, the operational window generally may define the boundaries of the well bore spacer system. The operational window may be defined as previously described in accordance with FIG. 1. By way of example, two or more boundary conditions may be used in defining the operational window of the spacer fluid system. In some embodiments, a two-dimensional triangular operational window may be defined. The boundary conditions used in defining the operational window may comprise, for example, weight ratio of weighting additive to water ("HWR") and weight ratio of viscosifier to water ("VWR"). Accordingly, a two-dimensional operational window may be defined as follows: Vertex 1 $(x_1, y_1)$, Vertex 2 $(x_2, y_2)$, and Vertex 3 $(x_3, y_3)$, wherein x is HWR and y VWR.

In accordance with present embodiments, the functional boundaries of the spacer fluid system may be used to define the operational window. By way of example, functional boundaries may include maximum VWR, minimum VWR, and maximum HWR. The maximum VWR may be the VWR above which the fluid system is unmixable. In one embodiment, the maximum VWR may be determined by maximizing the VWR until an unmixable concentration of the viscosity and water is achieved. The maximum VWR may be determined with a HWR of 0. Another functional boundary may include the minimum HWR. Minimum VWR may be the VWR below which solids cannot be suspended. In one embodiment, the minimum VWR may be determined by calculating the minimum amount of viscosifier required to suspend the heavyweight additive at low shear rate. Yet another functional boundary may include maximum HWR, which may be determined at minimum VWR. In one embodiment, maximum HWR may be determined by maximizing the HWR until an unmixable concentration of heavyweight additive in water (at minimum VWR) is achieved. FIG. 4 is a graphical representation of an example triangular operational window having three vertices defined by HWR and VWR. Vertex 1 is the maximum VWR, Vertex 2 is the minimum VWR at maximum HWR, and Vertex 3 is the minimum HWR at minimum VWR.

At step 10, the operational window may be divided into two or more sub-windows. This sub-division should increase the accuracy of the property prediction. By way of example, one or more points may be selected on edges of the operational windows that could be used to divide the operational window into sub-windows. For example, one pointed selected on the edge connecting Vertex 1 and Vertex 2, for example, on the midpoint of the edge. Another point may be selected on the edge connecting Vertex 2 and Vertex 3, for example, on the midpoint of the edge. Yet another point may be selected on the edge connecting Vertex 1 and 3, for example, on the midpoint of the edge. These three additional points may be used to divide the operational window into four sub-windows, as illustrated in FIG. 5.

At step 12, the example method may include collecting rheology data at the vertices of the sub-windows. Additional data may be collected related to one or more of the following properties: rheology, compressive strength, fluid loss, static gel strength, sedimentation, thickening time, free water, cement mechanical properties (e.g., Young's modulus, Poisson's ratio, specific heat, thermal conductivity, and post-set expansion), wettability, emulsion, break time, pH, post-set permeability, hydration time, post-set porosity, foam quality, permeability, expansion, water properties (e.g., pH, chlorides, bicarbonates, iron, tannin/lignins, carbonates, sulfates, magnesium, and calcium concentration), and fluid break time (e.g., for fracturing fluids). Data may be collected using standard laboratory techniques or other suitable methodologies. By way of example, the rheology data may be collected in accordance with the ANSI/API Recommended Practice 10B-2, Recommended Practice for Testing Well Cements, First Edition, July 2005. In some embodiments, historical data may be used so that additional laboratory testing may not be required.

At step 14, the example method may further include developing a model using Barycentric interpolation that includes predicted rheology data for a plurality of data points within the operational window of the fluid system. Density may also be determined for each of the data points within the operational window. The Barycentric interpolation may use the collected rheology data for the vertices of the sub-windows as the known data points in the interpolation. The interpolation technique may be adjusted to generate any number of data points within operational window.

Figure 3:
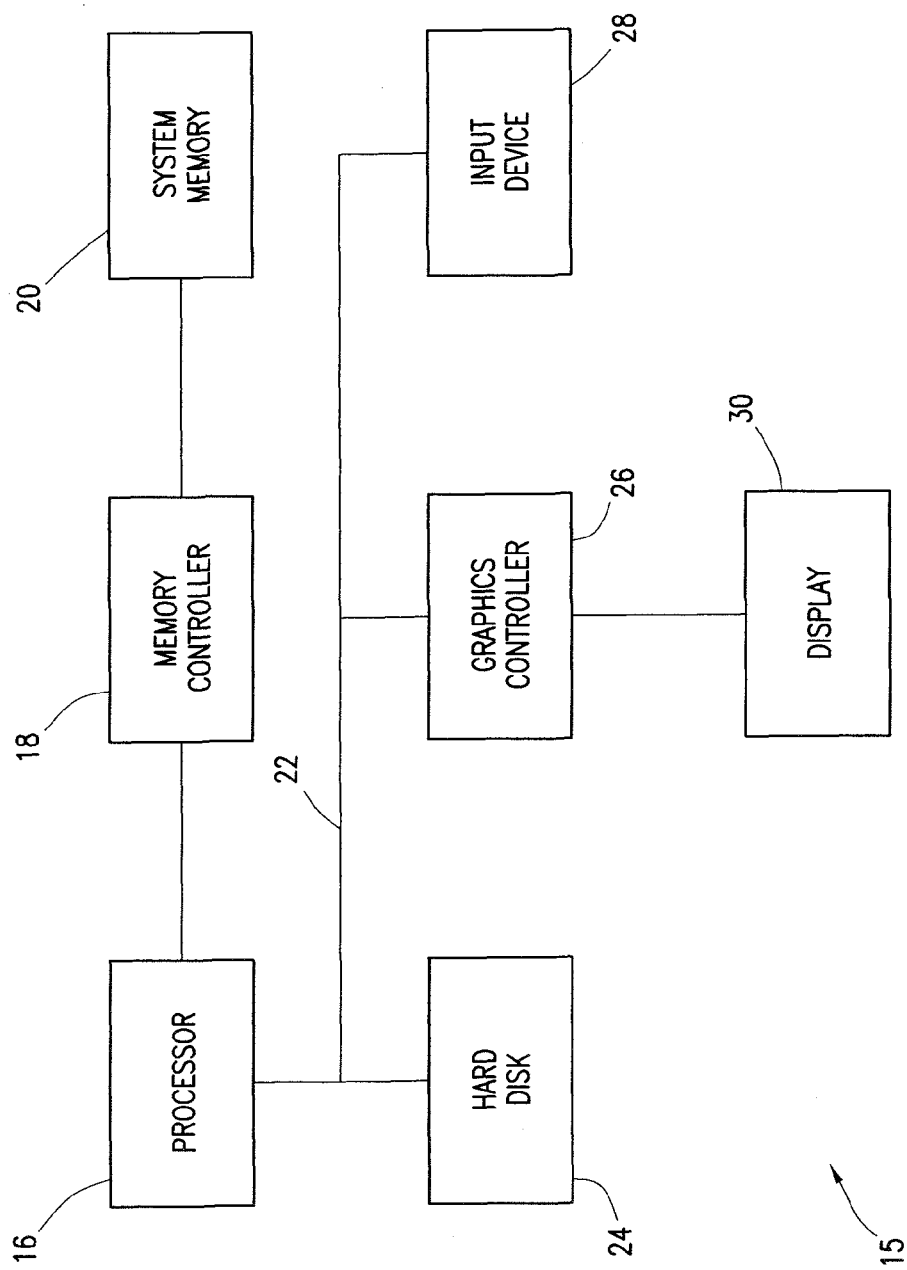
FIG. 3 is an example computer system that may be used in embodiments of the present techniques.

FIG. 3 is a block diagram of an exemplary computer system 15 that that may be used in performance of the techniques described herein. Software for performing the interpolations and other method steps may be stored in the computer system and/or on external computer readable media. Those of ordinary skill in the art will appreciate that the computer system 15 may comprise hardware elements including circuitry, software elements including computer code stored on a machine-readable medium or a combination of both hardware and software elements. Additionally, the blocks shown are but one example of blocks that may be implemented. A processor 16, such as a central processing unit or CPU, controls the overall operation of the computer system 15. The processor 16 may be connected to a memory controller 18, which may read data to and write data from a system memory 20. The memory controller 18 may have memory that includes a non-volatile memory region and a volatile memory region. The system memory 20 may be composed of a plurality of memory modules, as will be appreciated by one of ordinary skill in the art. In addition, the system memory 20 may include non-volatile and volatile portions. A system basic input-output system (BIOS) may be stored in a non-volatile portion of the system memory 20. The system BIOS may be adapted to control a start-up or boot process and to control the low-level operation of the computer system 15.

As illustrated, the processor 16 may be connected to at least one system bus 22, for example, to allow communication between the processor 16 and other system devices. The system bus may operate under a standard protocol such as a variation of the Peripheral Component Interconnect (PCI) bus or the like. In the exemplary embodiment shown in FIG. 3, the system bus 22 may connect the processor 16 to a hard disk drive 24, a graphics controller 26 and at least one input device 28. The hard disk drive 24 may provide non-volatile storage to data that is used by the computer system 15. The graphics controller 26 may in turn be connected to a display device 30, which provides an image to a user based on activities performed by the computer system 15. The computer system 15 may be programmed to perform operation and control methods of the present technique, including with regard to interpolation and comparison steps. The memory devices of the computer system 15, including the system memory 20 and the hard disk 24 may be tangible, machine-readable media that store computer-readable instructions to cause the processor 16 to perform a method according to an embodiment of the present techniques.

To facilitate a better understanding of the present invention, the following examples of certain aspects of some embodiments are given. In no way should the following examples be read to limit, or define, the entire scope of the invention.

EXAMPLE 1

A model was developed to predict fluid rheology for a well spacer system that comprised water, a heavyweight additive, and a viscosifier. The viscosifier used was SA-1015™ Suspending Agent, available from Halliburton Energy Services, Inc. The heavyweight additive used comprises 50 weight % cement kiln dust and 50 weight % barite. A dispersant (CFR-3TM dispersant, Halliburton Energy Services, Inc.) was also included in an amount of 0.4% by weight of the heavyweight additives. Depending on the source of the cement kiln dust, the dispersant may not be needed. The concentration of the dispersant can be varied to minimize cost. The model was developed by determining an operational window for the well spacer system, dividing the operational window into four sub-windows and then conducting six baseline rheology tests at the vertex of each sub-window. Each baseline rheology test included the particular fluid recipe for each vertex tested at 80° F., 130° F., and 180° F. Barycentric interpolation was then used to predict rheology data for multiple data points (approximately 30,000) within the operational window.

Figure 6:
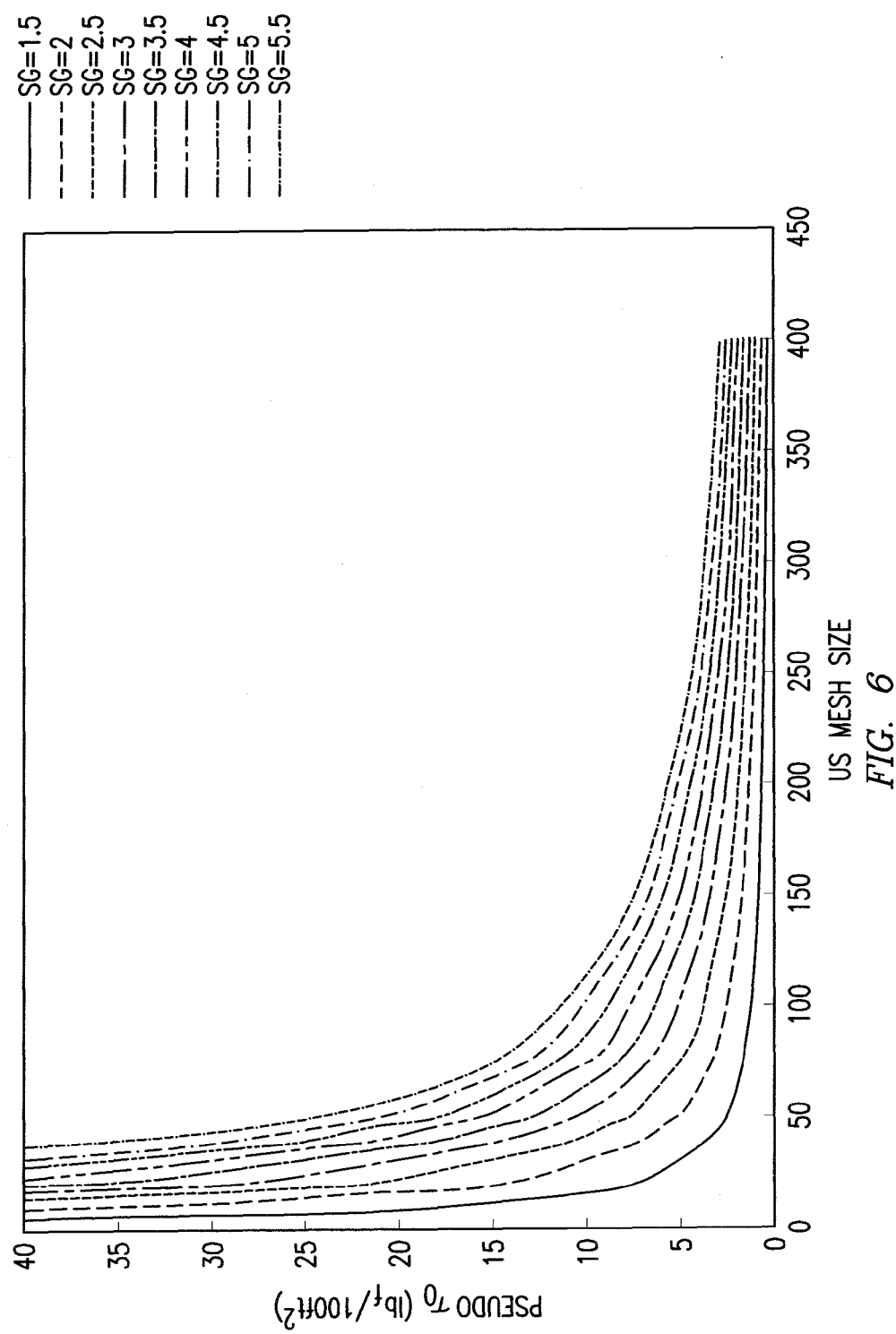
FIG. 6 is a particle suspension chart that may be used in determining an operational window in embodiments of the present techniques.

FIG. 4 is a graphical representation of the determined operational window. The functional boundaries of the well spacer system were used to define the operational window. The weight ratio of the heavyweight additive to water ("HWR") and the weight ratio of the viscosifier to water ("VWR") were used as the boundary conditions. The operational window was defined as follows: Vertex 1 $(x_1, y_1)$, Vertex 2 $(x_2, y_2)$, and Vertex 3 $(x_3, y_3)$, wherein $x_1$ is a HWR of 0, $y_1$ is maximum VWR, $x_2$ is maximum HWR of 0, $y_2$ is minimum VWR, $x_3$ is a HWR of 0, and $y_3$ is minimum VWR. The maximum VWR was determined at an HWR of 0 by maximizing the VWR until an unmixable concentration of the viscosity and water is achieved. The maximum VWR was determined to be 0.0125. The minimum VWR was determined by calculating the minimum amount of viscosifier required to suspend the heavyweight additive at low shear rate. FIG. 6 is a chart relating to material specific gravity and particle size that was created to aid in determining minimum VWR. The minimum VWR was determined to be 0.002. The maximum HWR was determined at minimum VWR by maximizing the HWR until an unmixable concentration of heavyweight additive in water was achieved. The maximum HWR was determined to be 1.565.

The operational window was then divided into four sub-windows, as shown on FIG. 5, represented as triangle α, triangle β, triangle γ, and triangle ρ. Points 4, 5, and 6 on FIG. 5 were determined by calculating the midpoints between Vertices 1 and 2, Vertices 2 and 3, and Vertices 1 and 3, respectively.

Baseline rheology tests were then conducted at the vertex of each sub-window, i.e., Vertex 1, Vertex 2, Vertex 3, Point 4, Point 5, and Point 6. Each baseline rheology test included the particular fluid recipe for each vertex tested at 80° F., 130° F., and 180° F. The rheology tests were conducting in accordance with ANSI/API Recommended Practice 10B-2, Recommended Practice for Testing Well Cements, First Edition, July 2005. The data for the six baseline rheology tests are provided in the table below.

TABLE 1

| Baseline Test | Temp. (° F.) | Viscometer RPM | | | | | |
|---|---|---|---|---|---|---|---|
| | | 300 | 200 | 100 | 60 | 30 | 6 | 3 |
| Vertex 1 | 80 | 80.5 | 78 | 74.5 | 70.5 | 66 | 53.95 | 50.25 |
| | 130 | 73.5 | 73 | 69.5 | 66.5 | 62.5 | 51.8 | 48.6 |
| | 180 | 65.5 | 64 | 61.5 | 60 | 56 | 48.2 | 45.75 |
| Vertex 2 | 80 | 68.5 | 55 | 39.5 | 32 | 25.5 | 16.7 | 14.8 |
| | 130 | 64 | 51 | 38 | 31 | 26 | 17.9 | 16.7 |
| | 180 | 72 | 58 | 43.5 | 36.5 | 31 | 26.75 | 22.6 |
| Vertex 3 | 80 | 11 | 9 | 8 | 7 | 7 | 6.6 | 6.45 |
| | 130 | 10 | 8.5 | 8 | 8 | 7.5 | 6.95 | 6.55 |
| | 180 | 10 | 9 | 8.5 | 8.5 | 8.5 | 7.9 | 7.45 |
| Point 4 | 80 | 90 | 83.5 | 75.5 | 71 | 66 | 54.2 | 50.55 |
| | 130 | 100 | 93 | 84 | 79 | 73 | 61.3 | 58 |
| | 180 | 90.5 | 86 | 78.5 | 73.5 | 69 | 61.35 | 59.85 |
| Point 5 | 80 | 27.5 | 23 | 18 | 16.5 | 13 | 10.05 | 9 |
| | 130 | 27 | 23 | 28 | 16 | 14 | 10.4 | 9.2 |
| | 180 | 27 | 23 | 19 | 16.5 | 14 | 10.7 | 10 |
| Point 6 | 80 | 42.5 | 40.5 | 38.5 | 36.5 | 34 | 28 | 25.75 |
| | 130 | 44.5 | 42.5 | 39.5 | 38 | 35.5 | 28.95 | 27.1 |
| | 180 | 46 | 45 | 42 | 40 | 37 | 32 | 30.4 |

After the data for the baseline rheology tests was collected, Barycentric interpolation was used to generate predicted rheological data for a plurality of data points within the operational window. Approximately 30,000 data points were generated by the interpolation. A Microsoft Excel spreadsheet was used to generate the predicted data. In addition to the predicted rheological data, the spreadsheet also determined density of the fluid corresponding to each data point and specific gravities of the materials used in the baseline rheology tests.

To more accurately predict a well spacer system ranging in density from 8.35 pounds per gallon to 16 pounds per gallon, two additional models were developed. Model 2 and Model 3 further included varying concentrations of barite in the weighting agent. Below are the weight ratios of cement kiln dust and barite that were used for each model:

Model 1—50 wt % cement kiln dust—50 wt % barite

Model 2—100 wt % cement kiln dust—0 wt % barite

Model 3—15 wt % cement kiln dust—85 wt % barite

EXAMPLE 2

Testing was conducted to evaluate the accuracy of the predicted rheological data generated using the models developed in Example 1. A spacer fluid was selected using Model 3 (15% cement kiln dust—85% barite) having an HWR of 1.06 and a VWR of 0.0031. The selected spacer fluid corresponds to a data point in Model 3. The selected spacer fluid from Model 3 had a density of 14 pounds per gallon and composition of the spacer fluid was water (125.57 grams), cement kiln dust (22.50 grams), barite (127.50 grams), viscosifier (0.43 grams) and dispersant (0.60 grams). The dispersant used was CFR-3™ cement friction reducer, available from Halliburton Energy Services, Inc. Rheology testing in accordance with ANSI/API Recommended Practice 10B-2, Recommended Practice for Testing Well Cements, First Edition, July 2005, was conducted at 80° F., 130° F., and 180° F. to compare the actual rheological data with the predicted rheological data from Model 3.

Table 2 below is a comparison of the predicted and actual rheological data for the selected spacer fluid.

TABLE 2

| | Temp. (° F.) | Viscometer RPM | | | | | |
|---|---|---|---|---|---|---|---|
| | | 300 | 200 | 100 | 60 | 30 | 6 | 3 |
| Actual | 80 | 51 | 43 | 36 | 33 | 29 | 23 | 13 |
| | | 44 | 36 | 32 | 29 | 23 | 22 | |
| | 130 | 47 | 42 | 37 | 34 | 31 | 25 | 11 |
| | | 42 | 36 | 33 | 30 | 25 | 23 | |
| | 180 | 48 | 43 | 38 | 36 | 33 | 28 | 23 |
| | | 43 | 38 | 35 | 32 | 27 | 25 | |
| Predicted | 80 | 52 | 46 | 37 | 33 | 29 | 22 | 20 |
| | 130 | 50 | 45 | 38 | 34 | 30 | 25 | 23 |
| | 180 | 49 | 44 | 37 | 34 | 31 | 25 | 23 |

Comparing the actual rheological data to the predicted rheological data from Model 3 shows very little variation, indicating that the model accurately predicted the rheological data for this particular data point.

EXAMPLE 3

Additional testing was conducted to evaluate the accuracy of the predicted rheological data generated using the models developed in Example 1. A spacer fluid was selected using Model 3 (15% cement kiln dust—85% barite) having an HWR of 1.06 and a VWR of 0.0031. The selected spacer fluid corresponds to a data point in Model 3. The selected spacer fluid from Model 3 had a density of 13.5 pounds per gallon and composition of the spacer fluid was water (141.54 grams), cement kiln dust (22.50 grams), barite (127.50 grams), viscosifier (0.43 grams) and dispersant (0.60 grams). The dispersant used was CFR-3TM cement friction reducer, available from Halliburton Energy Services, Inc. Rheology testing in accordance with ANSI/API Recommended Practice 10B-2, Recommended Practice for Testing Well Cements, First Edition, July 2005, was conducted at 80° F., 130° F., and 180° F. to compare the actual rheological data with the predicted rheological data from Model 3.

Table 3 below is a comparison of the predicted and actual rheological data for the selected spacer fluid.

TABLE 3

| | Temp. (° F.) | Viscometer RPM | | | | | |
|---|---|---|---|---|---|---|---|
| | | 300 | 200 | 100 | 60 | 30 | 6 | 3 |
| Actual | 80 | 40 | 36 | 31 | 28 | 26 | 20 | 16 |
| | | 36 | 30 | 28 | 25 | 20 | 18 | |
| | 130 | 39 | 35 | 30 | 28 | 25 | 18 | 13 |
| | | 35 | 30 | 28 | 25 | 20 | 18 | |
| | 180 | 38 | 34 | 30 | 28 | 26 | 21 | 19 |
| | | 35 | 30 | 28 | 26 | 21 | 19 | |
| Predicted | 80 | 43 | 37 | 30 | 27 | 24 | 18 | 17 |
| | 130 | 41 | 36 | 31 | 28 | 25 | 20 | 19 |
| | 180 | 40 | 36 | 31 | 28 | 25 | 20 | 19 |

Comparing the actual rheological data to the predicted rheological data from Model 3 shows very little variation, indicating that the model accurately predicted the rheological data for this particular data point.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Although individual embodiments are discussed, the invention covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present invention. If there is any conflict in the usages of a word or term in this specification and one or more patent(s) or other documents that may be incorporated herein by reference, the definitions that are consistent with this specification should be adopted.

What is claimed is:

1. A method of predicting fluid properties comprising:
    determining an operational window for a well bore fluid system, wherein three or more vertices are selected that define boundary conditions for the well bore fluid system, wherein the boundary conditions comprise a mass ratio of a weighting additive to water and a mass ratio of a viscosifier to water;
    dividing the operational window into sub-windows;
    conducting a lab test to collect data at the three or more vertices of the operational window; and
    developing a model with a computer system, wherein the model is based at least in part on the data, wherein the model comprises predicted properties for a plurality of data points within the operational window, wherein developing the model uses Barycentric interpolation;
    selecting a wellbore treatment fluid based on the model; and
    introducing the wellbore treatment fluid into a wellbore.

2. The method of claim 1, wherein determining the operational window comprises two or more boundary conditions for the well bore fluid system.

3. The method of claim 1, wherein the operational window comprises a triangular, two-dimensional window.

4. The method of claim 1, wherein the operational window is defined as follows: Vertex 1 $(x_1, y_1)$, Vertex 2 $(x_2, y_2)$, and Vertex 3 $(x_3, y_3)$, wherein x is a first boundary condition for the well bore fluid system and y is a second boundary condition for the well bore fluid system.

5. The method of claim 1, wherein the collected data includes data selected from the group consisting of rheology, compressive strength, fluid loss, static gel strength, sedimentation, thickening time, free water, Young's modulus, Poisson's ratio, specific heat, thermal conductivity, post-set expansion, wettability, emulsion, break time, pH, post-set permeability, hydration time, post-set porosity, and combinations thereof.

6. The method of claim 1, further comprising determining density of each of the plurality of data points within the operational window with the computer system.

7. The method of claim 1, wherein selecting the well bore treatment fluid comprising inputting one or more properties for the well bore treatment fluid, comparing the one or more properties to the predicted properties model; and outputting one or more data points from the model with the computer system.

8. The method of claim 1, wherein the well bore fluid system comprises a well bore spacer fluid system.

9. A method of predicting fluid properties comprising:
    determining an operational window for a well bore fluid system, wherein three or more vertices are selected that define boundary conditions for the well bore fluid system, wherein the boundary conditions comprise a mass ratio of a weighting additive to water and a mass ratio of a viscosifier to water;
    dividing the operational window into two or more sub-windows;
    collecting data at the three or more vertices of each of the two or more sub-windows using laboratory techniques;
    developing a model comprising predicted properties for a plurality of data points within the operational window, wherein developing the model uses Barycentric interpolation, wherein the predicted properties comprise density;
    selecting a well bore treatment fluid using the model, wherein selecting the well bore treatment fluid comprises inputting properties of the well bore treatment fluid;
    refining the wellbore treatment fluid using simulation and/or laboratory testing; and
    introducing the refined wellbore treatment fluid into a wellbore.

10. The method of claim 9, wherein the operational window comprises a triangular, two-dimensional window.

11. The method of claim 9, wherein the operational window is defined as follows: Vertex 1 $(x_1, y_1)$, Vertex 2 $(x_2, y_2)$, and Vertex 3 $(x_3, y_3)$, wherein x is a first boundary condition for the well bore fluid system and y is a second boundary condition for the well bore fluid system.

12. The method of claim 9, wherein the collected data includes data selected from the group consisting of rheology, compressive strength, fluid loss, static gel strength, sedimentation, thickening time, free water, Young's modulus, Poisson's ratio, specific heat, thermal conductivity, post-set expansion, wettability, emulsion, break time, pH, post-set permeability, hydration time, post-set porosity, and combinations thereof.

13. The method of claim 9, further comprising determining density of each of the plurality of data points within the operational window with the computer system.

14. The method of claim 9, wherein the well bore fluid system comprises a well bore spacer fluid system.

* * * * *